(12) United States Patent
Giuberti et al.

(10) Patent No.: US 10,993,640 B2
(45) Date of Patent: May 4, 2021

(54) SYSTEM AND METHOD FOR MONITORING THE MOVEMENT OF A PART OF A HUMAN BODY

(71) Applicant: TELECOM ITALIA S.p.A., Milan (IT)

(72) Inventors: Matteo Giuberti, Parma (IT); Gianluigi Ferrari, Parma (IT); Alessandro Mauro, Oggebbio (IT); Corrado Azzaro, Oggebbio (IT); Giovanni Albani, Oggebbio (IT); Roberto Nerino, Turin (IT); Laura Contin, Turin (IT)

(73) Assignee: TELECOM ITALIA S.p.A., Milan (IT)

( * ) Notice: Subject to any disclaimer, the term of this patent is extended or adjusted under 35 U.S.C. 154(b) by 235 days.

(21) Appl. No.: 15/539,955

(22) PCT Filed: Dec. 30, 2014

(86) PCT No.: PCT/EP2014/079466
§ 371 (c)(1),
(2) Date: Jun. 26, 2017

(87) PCT Pub. No.: WO2016/107653
PCT Pub. Date: Jul. 7, 2016

(65) Prior Publication Data
US 2017/0340248 A1    Nov. 30, 2017

(51) Int. Cl.
*A61B 5/11*        (2006.01)
*A61B 5/00*        (2006.01)

(52) U.S. Cl.
CPC ......... *A61B 5/1124* (2013.01); *A61B 5/0022* (2013.01); *A61B 5/11* (2013.01);
(Continued)

(58) Field of Classification Search
CPC ... A61B 5/1124; A61B 5/1121; A61B 5/1122; A61B 5/1123; A61B 5/11; A61B 5/1107;
(Continued)

(56) References Cited

U.S. PATENT DOCUMENTS

| | | | |
|---|---|---|---|
| 9,068,843 B1 * | 6/2015 | Sohn | G06F 3/03 |
| 2005/0088296 A1 * | 4/2005 | Lee | G08B 21/02 |
| | | | 340/539.12 |

(Continued)

OTHER PUBLICATIONS

J.B. Kuipers "Quaternions and Rotation Sequences: A Primer with Applications to Orbits, Aerospace and Virtual Reality" Princeton, NJ, USA, Princeton University Press, 1999, 353 pages.
(Continued)

*Primary Examiner* — Daniel L Cerioni
*Assistant Examiner* — Avery M Foley
(74) *Attorney, Agent, or Firm* — Oblon, McClelland, Maier & Neustadt, L.L.P.

(57) ABSTRACT

The movement of a part of human body, e.g. a limb, is monitored. The movement includes N iterated rotations in a plane. A sensing device is fixed to the limb and provides data indicative of the limb movement. These data are processed to generate a rotation signal. Then, portions of the rotation signal corresponding to each movement iteration are identified. To this purpose, a plurality of null-velocity instants is identified, wherein the angular velocity of the sensing device is null. Then, each null-velocity instant is classified as a candidate start/end time or a candidate peak time. Then, a start time, end time and peak time for each iteration are determined as a combination of two candidate start/end times and a candidate peak time that fulfils certain conditions on the values of the rotation signal in correspondence of candidate start/end times and candidate peak times.

19 Claims, 8 Drawing Sheets

(52) U.S. Cl.
CPC .......... *A61B 5/1121* (2013.01); *A61B 5/4082* (2013.01); *A61B 5/6828* (2013.01); *A61B 5/7225* (2013.01); *A61B 5/7264* (2013.01); *A61B 2562/0219* (2013.01); *A61B 2562/0223* (2013.01)

(58) Field of Classification Search
CPC ... A61B 5/1114; A61B 5/1118; A61B 5/4082; A61B 5/6813; A61B 5/6802; A61B 5/6828; A61B 5/7225; A61B 5/7264; A61B 2562/0219; A61B 2562/0223
See application file for complete search history.

(56) References Cited

U.S. PATENT DOCUMENTS

| | | | |
|---|---|---|---|
| 2012/0253216 A1 | 10/2012 | Fu et al. | |
| 2013/0131555 A1* | 5/2013 | Hook | A61B 5/112 600/595 |
| 2016/0015972 A1* | 1/2016 | Hyde | A61N 1/36031 607/48 |
| 2017/0016993 A1* | 1/2017 | Liu | G01S 19/14 |
| 2017/0188895 A1* | 7/2017 | Nathan | A61B 5/1122 |

OTHER PUBLICATIONS

International Search Report dated Aug. 4, 2015, in PCT/EP2014/079466 filed Dec. 30, 2014.

Giuberti, "Inertial Sensing for Human Motion Analysis: Processing, Technologies, and Applications", Universita Di Parma, (2014), 176 pages, XP002742615.

Giuberti et al., "Linking UPDRS Scores and Kinematic Variables in the Leg Agility Task of Parkinsonians", 2014 11$^{th}$ International Conference on Wearable and Implantable Body Sensor Networks, (2014), pp. 115-120, XP032620734.

Giuberti et al., "On the Characterization of Leg Agility in Patients with Parkinson's Disease", 2013 IEEE International Conference on Body Sensor Networks,(2013), 6 pages, XP032474404.

Najafi et al., "Measurement of Stand-Sit and Sit-Stand Transitions Using a Miniature Gyroscope and Its Application in Fall Risk Evaluation in the Elderly", IEEE Transactions on Biomedical Engineering, vol. 49, No. 8, (2002), pp. 843-851.

Aminian et al.. "Spatia-temporal parameters of gait measured by an ambulatory system using miniature gyroscopes", Journal of Biomechanics, vol. 35, No. 5, (2002), pp. 689-699.

Madgwick, "An efficient orientation filter for inertial and inertial/magnetic sensor arrays", Department of Mechanical Engineering, (2010), pp. 1-32, (16 Sheets).

* cited by examiner

SYSTEM AND METHOD FOR MONITORING THE MOVEMENT OF A PART OF A HUMAN BODY

TECHNICAL FIELD

The present invention generally relates to the field of human body movement monitoring systems and methods. In particular, the present invention relates to a method and system for monitoring the movement of a part of a human body, such as a limb.

BACKGROUND ART

As known, motor difficulties (such as slowness and/or interruptions in the execution of some movements, tremors and rigidity) are amongst the main symptoms of many neurodegenerative diseases, such as the Parkinson's disease. Nowadays, the pathology severity of the Parkinson's Disease (PD) patients is typically tested and evaluated through simple functional tasks/exercises, universally accepted as a standard by the neurologists' community. Every task is properly evaluated by using a discrete scale, the Unified Parkinson Disease Rating Scale (UPDRS), whose ratings range from 0 (when the task is performed normally) to 4 (when the pathology is so severe that the PD patient is not able to perform the task). Provided that PD patients typically suffer from motion impairments, a section of UPDRS focuses specifically on the evaluation of motor tasks.

One of these standard motor tasks is the so-called Leg Agility task. Generally, for executing this task, the patient is asked to sit on a chair with a rigid backrest and armrests. The patient should keep both his/her feet on the floor comfortably. The patient is then asked to repeatedly lift up a foot as high and as fast as possible and then pull it down. Ten movement iterations per leg are generally required to accomplish the task.

Typically, the patient executes the motor tasks (including the Leg Agility task) in clinic or hospital scenarios. In particular, the patient performs the tasks at the presence of an examiner (e.g. a neurologist or specialized personnel) who observes the patient and, based on her/his personal perception and experience, provides a subjective evaluation of the patient's motor skills and then assigns an UPDRS score thereto.

Techniques are also known which provide an objective, quantitative evaluation of the movements of a person.

In particular, B. Najafi et al. "Measurement of stand-sit and sit-stand transitions using a miniature gyroscope and its application in fall risk evaluation in the elderly", IEEE transactions on biomedical engineering, Vol. 49, No. 8, pp. 843-851, Aug. 2002, describes a method for evaluating postural transitions, in particular for measuring the time of sit-to-stand and stand-to-sit transitions and their duration using a miniature gyroscope attached to the chest of the patient and a portable recorder placed on the waist. The method is based on the discrete wavelets transform and provides three parameters: average and standard deviation of transition duration and occurrence of abnormal successive transitions (number of attempts to have a successful transition).

K. Aminian et. al. "Spatio-temporal parameters of gait measured by an ambulatory system using miniature gyroscopes", Journal of Biomechanics, Vol. 35, No. 5, pp. 689-699, May 2002 describes an ambulatory system for estimation of spatio-temporal parameters during long periods of walking, which uses a gyroscope attached to the shank of the user. This method is based on wavelets analysis to compute the values of temporal gait parameters from the angular velocity of the lower limbs. Based on a mechanical model, the medio-lateral rotation of the lower limbs during stance and swing, the stride length and velocity are estimated by integration of the angular velocity.

SUMMARY OF THE INVENTION

The inventors have noticed that motor skill evaluation (including the evaluation of the Leg Agility task) aimed e.g. at assigning an UPDRS score to patients affected by the Parkinson's disease shall be frequently performed, e.g. once a day or more. This allows continuously monitoring the severity of the pathology, and ultimately allows to define and tune the drug dosage for the patient.

To this purpose, an automated motor skill evaluation would be desirable, namely an evaluation that does not require the intervention of any examiner observing the patient and personally providing an evaluation of his/her motor skills. This would allow the patient to perform the motor skill evaluation as often as necessary in an autonomous way at his/her premises, without the need to go to a clinic or hospital. Furthermore, an automated motor skill evaluation would advantageously provide objective results, thereby allowing to avoid the result uncertainty which inherently derives from subjective evaluations.

Though in principle the above described technique of B. Najafi et al. for the postural transition analysis and the above described technique of K. Aminian et al. for the gait analysis provide an objective and automated quantitative evaluation of the user's movements, the inventors have noticed that such techniques are not applicable for evaluating the movements of patients affected by the motor difficulties typical of a neurodegenerative disease such as the Parkinson's disease.

When a patient performs e.g. the Leg Agility task, indeed, the movement of his/her leg is not fluid at all, but it typically exhibits several anomalies such as tremors, interruptions (also termed "freezing") and hesitations, which the wavelets analysis carried out by those known techniques is not able to handle. In particular, such known techniques require the identification of absolute minima and maxima of either the trunk tilt (in the postural transition analysis technique of B. Najafi et al.) or the shank angular velocity (in the gait analysis technique of K. Aminian et al.). Such identification may however be problematic in case of movement performed by a PD (Parkinson's disease) patient, since the above movement anomalies may result in relative maxima or minima which the wavelets analysis cannot filter out and which may be therefore erroneously considered as the absolute ones, thereby leading to wrong results.

Moreover, the technique of K. Aminian et al. for the gait analysis requires assuming a maximum duration of each step. This is however not feasible in case of the Leg Agility task (especially when it is performed by a patient with motor difficulties), since the maximum duration of each iteration of the leg movement is not predictable (on the contrary, it is one of the kinematic quantities to be measured).

In view of the above, the inventors have tackled the problem of providing a method and system for monitoring the movement of a part of a human body which overcomes the aforesaid drawbacks.

In particular, the inventors have tackled the problem of providing a method and system for monitoring the movement of a part of a human body such as a limb (in particular, but not exclusively, a leg) which is capable of providing reliable and accurate results even when the movement exhibits the above described anomalies that are typical of a patient affected by a neurodegenerative disease, and which does not require any specific assumption on the movement maximum duration.

According to the present invention, the above problems are solved by providing a sensing device cooperating with the limb so as to provide data indicative of the limb movement. The limb movements comprises N iterations of a rotation in a plane xy. In case of the Leg Agility task, the sensing device is attached to the thigh of the patient, who repeatedly lifts up and pulls down her/his foot while sitting on a chair, so that her/his thigh rotates on a substantially vertical plane (lateral displacement of the leg is negligible). The data provided by the sensing device are processed so as to generate a signal (also termed "rotation signal" in the following description and in the claims) indicative of the limb rotation in the plane xy. Further, according to the present invention, the rotation signal is segmented, namely signal portions are identified corresponding to respective iterations of the limb rotation in the plane xy. Each signal portion is determined by determining its start time (namely the instant in which the patient starts lifting his/her foot), peak time (namely the instant in which the patient's leg reaches its maximum height) and end time (namely the instant in which the patient's foot is brought back to the floor). In order to determine start time, end time and peak time, firstly the instants are determined in which the angular velocity of the limb in the plane xy is null. It shall be noticed that such instants comprise all the instants in which the limb is still, included those in which the patient movement exhibits anomalies such as freezing or hesitation. Then, a set of candidate start/end times and a set of candidate peak times are identified amongst such null-velocity instants. To this purpose, conditions are checked on relative values of the rotation signal in correspondence of the null-velocity instants. Then, start time, end time and peak time of an iteration are determined as the combination of two candidate start/end times and one candidate peak time that fulfils one or more conditions on the values of the rotation signal in correspondence of the candidate start/end times and candidate peak times.

The determined start time, end time and peak time—and the values of the rotation signal in correspondence of the determined start time, end time and peak time—may then be used for calculating one or more kinematic quantities (e.g. speed, displacement, etc.) quantitatively describing the movement of the limb within that iteration.

Thus, the rotation signal may be properly segmented, namely each single iteration of the leg movement may be properly identified and isolated. Proper identification of start time, end time and peak time of each iteration may be indeed carried out, even if the rotation signal—in addition to the absolute minima and maxima corresponding to the leg start position, leg end position and leg maximum-height position—comprises other null-velocity points (e.g. local minima and maxima) due to anomalies of the leg movement. Hence, the values of the kinematic quantities calculated based on such start time, end time and peak time are very accurate and reliable, even when the movement exhibits the above described anomalies that are typical of a patient affected by a neurodegenerative disease. Further, no specific assumption on the movement maximum duration shall be made. The rotation signal may be segmented and accurate results may be provided on a wide range of periodic or quasi-periodic movements, including those whose maximum period is not predictable.

According to a first aspect, the present invention provides a method for monitoring the movement of a part of a human body, the movement comprising a number N of iterations of a rotation of the part of human body in a plane xy, the method comprising:

providing data indicative of the movement of the part of human body and processing the data so as to generate a rotation signal $\theta(t)$ indicative of the rotation of the part of human body in the plane xy; and
  identifying a portion of the rotation signal $\theta(t)$ corresponding to a respective iteration of the rotation of the part of human body in the plane xy by determining a start time $t_S$, an end time $t_E$ and a peak time $t_P$ of the respective iteration, the determining comprising:
    determining a plurality of null-velocity instants $t^*$ wherein an angular velocity of the part of a human body 2 in the plane xy is substantially null;
    determining, amongst the plurality of null-velocity instants $t^*$, a set of candidate start/end times and a set of candidate peak times on the basis of at least one condition on relative values of the rotation signal $\theta(t)$ in correspondence of the plurality of null-velocity instants $t^*$; and
    determining the start time $t_S$, the end time $t_E$ and the peak time $t_P$ as a combination of two candidate start/end times and a candidate peak time that fulfils at least one condition on values of the rotation signal $\theta(t)$ in correspondence of the candidate start/end times and the candidate peak times.

Preferably, the data provided by the sensing device comprise first inertial data provided by an accelerometer of a sensing device cooperating with the part of human body, second inertial data provided by a gyroscope of the sensing device, and magnetic data provided by a magnetometer of the sensing device.

Preferably, if a norm of the acceleration detected by the accelerometer is lower than a predetermined threshold, the method comprises processing the first inertial data and the magnetic data to generate the rotation signal $\theta(t)$; moreover, if a norm of the acceleration detected by the accelerometer is higher than the predetermined threshold, the method comprises processing the second inertial data to generate the rotation signal $\theta(t)$.

Preferably, processing the data so as to generate the rotation signal $\theta(t)$ comprises filtering the data through an orientation estimation filter providing as outPut a 4-dimensional array representing an orientation of the sensing device in a 3D space, and deriving the rotation signal from the 4-dimensional array.

Preferably, determining the set of candidate start/end times and the set of candidate peak times comprises classifying each null-velocity instant $t^*(i)$ as either a candidate start/end time or a candidate peak time by comparing the value of the rotation signal $\theta(t)$ in correspondence of the null-velocity instant $t^*(i)$ to be classified with the value of the rotation signal $\theta(t)$ in correspondence of a further null-velocity instant preceding or succeeding the null-velocity instant $t^*(i)$ to be classified.

Preferably, determining the set of candidate peak times amongst the plurality of null-velocity instants $t^*$ comprises classifying the null-velocity instant $t^*(i)$ as a candidate peak time if $\theta(t^*(i)) > \theta(t^*(i-1))$ and $\theta(t^*(i)) > \theta(t^*(i+1))$.

Preferably, determining the set of candidate start/end times amongst the plurality of null-velocity instants $t^*$ comprises classifying the null-velocity instant $t^*(i)$ as a candidate start/end time if:

$\theta(t^*(i)) < \theta(t^*(i+1))$, in case the null-velocity instant $t^*(i)$ is the first null-velocity instant;

$\theta(t^*(i)) < \theta(t^*(i-1))$, in case the null-velocity instant $t^*(i)$ is the last null-velocity instant identified; and $\theta(t^*(i)) < \theta(t^*(i-1))$ and $\theta(t^*(i)) < \theta(t^*(i+1))$ for any other null-velocity instant $t^*(i)$ identified subsequently to the last determined end time.

Preferably, determining the start time $t_S$, the end time $t_E$ and the peak time $t_P$ comprises finding a combination of two candidate start/end times and a candidate peak time whose chronological order is such that the peak time $t_P$ lies between the start time $t_S$ and the end time $t_E$.

Preferably, determining the start time $t_S$, the end time $t_E$ and the peak time $t_P$ comprises finding a combination of two candidate start/end times and a candidate peak time which fulfils the following condition:

$$\theta(t_P) - \frac{\theta(t_S) + \theta(t_E)}{2} \geq c_1$$

where c1 is a first threshold.

Preferably, determining the start time $t_S$, the end time $t_E$ and the peak time $t_P$ comprises finding a combination of two candidate start/end times which fulfils the following condition:

$$(\theta(t_S) - \theta(t_E)) \leq c_2$$

where c2 is a second threshold.

Preferably, identifying a portion of the rotation signal $\theta(t)$ corresponding to a respective iteration of the rotation in the plane xy is started while the respective iteration is being executed by the part of human body, after the end time for the iteration preceding the respective iteration has been determined.

Preferably, determining the plurality of null-velocity instants t* comprises forming a set of null-velocity instants t* subsequent to the end time of the preceding iteration, and updating it by adding thereto each new null-velocity instant t* subsequent to the end time of the preceding iteration, when the new null-velocity instant t* is identified; determining the set of candidate start/end times and the set of candidate peak times comprises classifying the new null-velocity instant t* as a candidate start/end time or as a candidate peak time, when the new null-velocity instant t* is identified; and determining the start time $t_S$, the end time $t_E$ and the peak time $t_P$ comprises seeking for the combination of two candidate start/end times and one candidate peak time which fulfils the at least one condition, when the new null-velocity instant t* is classified as either a candidate start/end time or a candidate peak time.

Preferably, if the sensing device stops providing the data indicative of the movement, the step of determining the start time $t_S$, the end time $t_E$ and the peak time $t_P$ is stopped and the null-velocity instants t* subsequent to the end time of the preceding iteration are discarded.

Preferably, if the start time $t_S$, the end time $t_E$ and the peak time $t_P$ are not determined before a predetermined time gap has lapsed since the end time of the preceding iteration, the step of determining the start time $t_S$, the end time $t_E$ and the peak time $t_P$ is stopped and the null-velocity instants t* subsequent to the end time of the preceding iteration are discarded.

According to a second aspect, the present invention provides a system for monitoring the movement of a part of a human body, the movement comprising a number N of iterations of a rotation of the part of human body in a plane xy, the system comprising:

a sensing device suitable for cooperating with the part of the human body and for providing data indicative of the movement of the part of human body; and a processing unit configured to process the data so as to generate a rotation signal $\theta(t)$ indicative of the rotation of the part of human body in the plane xy and to identify a portion of the rotation signal $\theta(t)$ corresponding to a respective iteration of the rotation in the plane xy by determining a start time $t_S$, an end time $t_E$ and a peak time $t_P$ of the respective iteration, the determining comprising:

determining a plurality of null-velocity instants t* wherein an angular velocity of the part of a human body 2 in the plane (xy) is substantially null;

determining, amongst the plurality of null-velocity instants t*, a set of candidate start/end times and a set of candidate peak times on the basis of at least one condition on relative values of the rotation signal $\theta(t)$ in correspondence of the plurality of null-velocity instants t*; and determining the start time $t_S$, the end time $t_E$ and the peak time $t_P$ as a combination of two candidate start/end times and a candidate peak time that fulfils at least one condition on values of the rotation signal $\theta(t)$ in correspondence of the candidate start/end times and the candidate peak times.

According to a third aspect, the present invention provides a computer program product loadable in the memory of at least one computer and including software code portions for performing the steps of the method as set forth above, when the product is run on the at least one computer.

BRIEF DESCRIPTION OF THE DRAWINGS

The present invention will become clearer from the following detailed description, given by way of example and not of limitation, to be read with reference to the accompanying drawings, wherein.

DETAILED DESCRIPTION OF PREFERRED EMBODIMENTS OF THE INVENTION

Figure 1:
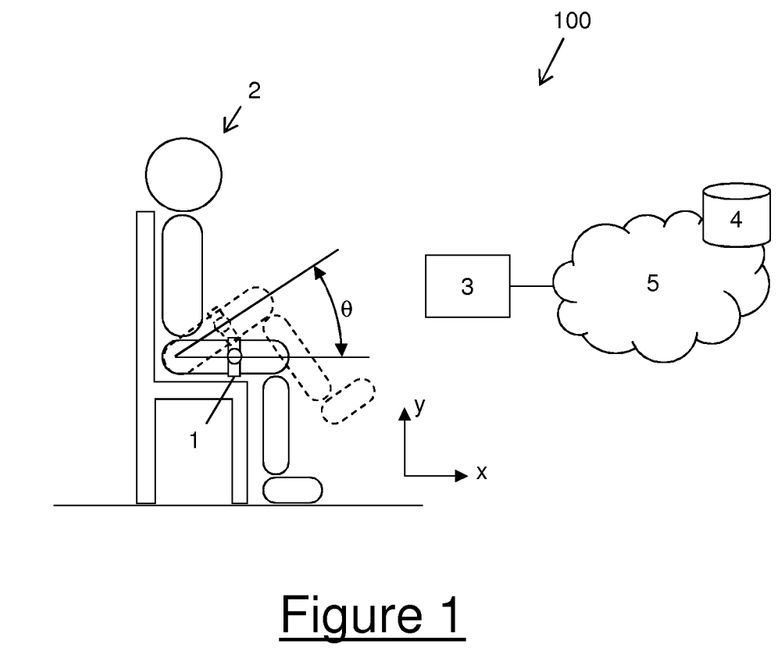
FIG. 1 schematically shows a system according to an embodiment of the present invention.

With reference to FIG. 1, a system 100 for monitoring the movement of a part of a human body such as a limb will be now described in detail. The system 100 preferably comprises a sensing device 1 suitable for being fixed to the limb of a user 2, to sense the movements of the limb and to provide data indicative of the movement of the limb. The sensing device 1 preferably comprises an accelerometer and/or a gyroscope. Optionally, the sensing device 1 also comprises a magnetometer. According to a particularly preferred variant, the sensing device 1 is an inertial sensor. As known, an inertial sensor comprises at least one accelerometer (typically, a triaxial accelerometer) suitable for detecting accelerations along the three axis of an arbitrarily chosen coordinate system, at least one gyroscope (typically, a triaxial gyroscope) suitable for detecting changes in rotational attributes (such as pitch, roll and yaw) with reference to an arbitrarily chosen coordinate system and, optionally, a magnetometer, which is mostly used to assist calibration against orientation drifts. According to such variant, the sensing device 1 is therefore configured to provide inertial data (and optionally magnetic data) indicative of the movement of the limb.

As mentioned above, the sensing device 1 is a wearable device, namely it is suitable for being fixed to the limb of the user 2. To this purpose, the sensing device 1 may be provided with fixing means such as an elastic band. The fixing means preferably retain the sensing device 1 against the user's skin with a certain pressure, so as to prevent spurious movements of the sensing device 1 relative to the limb which may impair the measurement accuracy. For instance, in case the system 100 is used for evaluating the Leg Agility task, the sensing device 1 is preferably fixed to a thigh of the user 2. This may be done by means of an elastic band retaining the sensing device 1 against the thigh of the user 2. Alternatively, the sensing device 1 may be placed in the pants' pocket, provided it is kept in contact with the thigh of the user 2.

Though a single sensing device 1 is shown in FIG. 1, the system 100 may include more than one sensing device 1. In particular, if a task requires moving more than one limb, a separate sensing device is preferably provided for each limb. For instance, in case of the Leg Agility task, both legs shall be moved. Hence, a separate sensing device 1 may be provided for each leg.

The system 100 also preferably comprises a processing unit 3. The sensing device 1 is preferably connected to the processing unit 3 so as to transmits the generated inertial data (and the optionally generated magnetic data) thereto. The connection between sensing device 1 and processing unit 3 is preferably a wireless connection, for instance a short range wireless connection. Exemplary technologies for implementing such connection are Bluetooth, Zigbee, etc. The processing unit 3 is preferably comprised in a local device which is located at the premises of the user 2. For instance, the local device may be a smartPhone, a tablet, a PC or so on. According to other embodiments (not shown in the drawings), the processing unit 3 is part of a cloud computing architecture to which the sensing device 1 transmits the generated inertial data (and the optionally generated magnetic data), e.g. via a wireless router.

The system 100 is preferably connected to a remote database 4 via a communication network 5.

Figure 2:
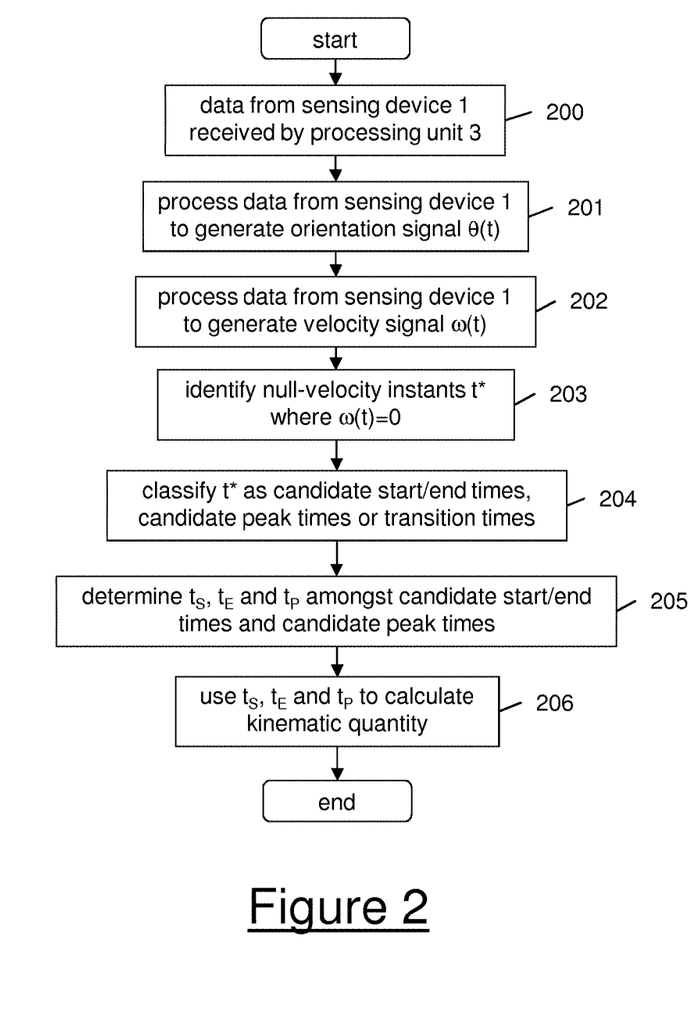
FIG. 2 is a flow chart of the operation of the system of FIG. 1, according to an embodiment of the present invention.

The operation of the system 100 will be now described in detail, with reference to the flow chart of FIG. 2. Hereinafter, by way of non limiting example, reference will be made to the above described Leg Agility task.

As the user 2 starts performing the Leg Agility task, she/he starts repeatedly lifting up and pulling down her/his leg while sitting on a chair, as schematically depicted in FIG. 1. Hence, the leg rotates substantially on a plane xy (also schematically depicted in FIG. 1), while lateral displacements of the leg (namely, displacements in the direction perpendicular to the plane xy) are substantially negligible. Since the user 2 repeats the leg movement several times (typically ten times, for accomplishing the task), the leg rotates back and forth between a first position (foot resting against the floor, minimum tilt of the thigh relative to the floor) and a second position (leg at its maximum height, maximum tilt of the thigh relative to the floor).

Since the sensing device 1 is fixed to the thigh of the user 2, the thigh rotations result in changes of the planar rotation of the sensing device 1 in the plane xy. In the present description, the expression "planar rotation" will designate the angular position of the sensing device 1 in the plane xy, namely the angular width of the rotation that is needed to move the sensing device 1 in the plane xy from a reference position (sensing device substantially lying on the x axis) to its current position. The sensing device 1 accordingly generates inertial data (and optionally magnetic data), which reflect the thigh rotations back and forth between a first position (minimum tilt position) and a second position (maximum tilt position).

With reference now to the flow chart of FIG. 2, during a first step 200 the inertial data (and optionally the magnetic data) generated by the sensing device 1 are transmitted to the processing unit 3.

During a second step 201, the processing unit 3 preferably processes the received inertial data (and optionally the received magnetic data) so as to generate a signal $\theta(t)$ (also termed herein after "rotation signal") indicative of the planar rotation of the tight (and hence of the sensing device 1) in the plane xy. For processing slow movements of the user's thigh, the processing unit 3 preferably uses the inertial data provided by the accelerometer of the sensing device 1 (and optionally the magnetic data provided by the magnetometer of the sensing device 1) to generate the rotation signal $\theta(t)$. For processing fast and short movements of the user's thigh, the processing unit 3 preferably uses the inertial data provided by the gyroscope of the sensing device 1. In particular, fast movements can be identified for example by setting a threshold on the acceleration norm, while a second threshold can be used to limit the use of gyroscope data. Either these thresholds are usually defined in a heuristic way, depending on the type of movement, noise of sensors, etc.

It shall be noticed that implementing the sensing device 1 as an inertial sensor comprising the combination of an accelerometer, a gyroscope and a magnetometer (instead of, for instance, a gyroscope only) is particularly advantageous. In fact, using a gyroscope alone cannot provide a reliable long term measurement of planar rotation due to measurement errors caused by the noise of the gyroscope. An accelerometer and a magnetometer that measure earth's gravitational and the magnetic field, respectively, provide an absolute reference of planar rotation. However accelerometer and magnetometer can also be subjected to high levels of noise; for example, accelerations due to motion may corrupt measured direction of gravity and the presence of ferromagnetic objects can introduce distortion in the measured gravity field. Hence, implementing the sensing device 1 as an inertial sensor comprising the combination of an accelerometer, a gyroscope and a magnetometer advantageously guarantees a heterogeneous source of data and, consequently, improves the robustness of the estimation of the rotation signal $\theta(t)$.

Step 201 preferably comprises filtering in real-time the data received from the sensing device 1 through an orientation estimation filter included in the processing unit 3. According to an alternative embodiment, the orientation estimation filter can be included in the sensing device 1. In the latter case, step 201 can be performed by the sensing device 1 itself, which accordingly provides to the processing unit 3 the rotation signal θ(t), instead of raw data. In both cases, the orientation estimation filter may be of a known type, such as for instance the filter described in S. O. H. Madgwick, "An efficient orientation filter for inertial and inertial/magnetic sensor arrays", Department of Mechanical Engineering, University of Bristol, UK, Tech. Rep., April 2010, available at the following URL: httP://www.x-io.co.uk/res/doc/madgwick internal report.pdf This is however not limiting, since other known filters may be used, e.g. a Kalman filter. As known, an orientation estimation filter outPuts a quaternion (see J. B. Kuipers, "Quaternions and Rotation Sequences: A Primer with Applications to Orbits, Aerospace and Virtual Reality", Princeton, N.J., USA, Princeton University Press, 1999), namely a 4-dimensional array representing the orientation of the sensing device 1 in a 3D space, from which the rotation signal θ(t) is directly derived in a known way.

Figure 3A:
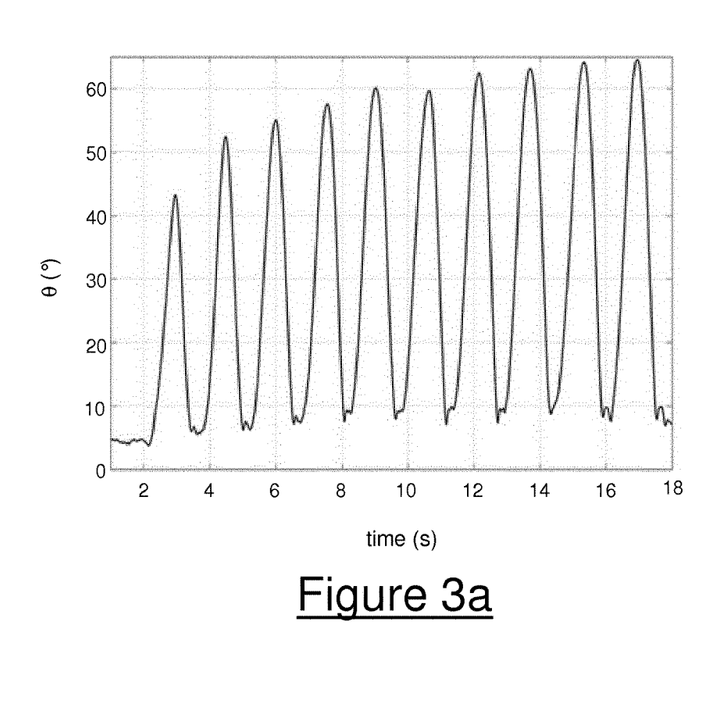
FIGS. 3a and 3b respectively show an exemplary rotation signal and an exemplary velocity signal relating to the sensing device of FIG. 1.

FIG. 3a schematically shows an exemplary rotation signal θ(t) as provided upon execution of step 201, relating to a sensing device 1 fixed to the thigh of a user 2 executing ten movement iterations of her/his thigh. The rotation signal θ(t) of FIG. 3a exhibits ten maxima, each one corresponding to the maximum tilt position reached at a respective iteration of the leg movement. In principle (namely, in a healthy user), the rotation signal θ(t) should also comprise ten sharp minima corresponding to the minimum tilt position reached by the thigh at the various iterations of the leg movement. A periodic, substantially sinusoidal rotation signal θ(t) with sharp maxima and minima would be therefore provided. However, as discussed above, the movement of a patient with motor difficulties is typically affected by several anomalies. The rotation signal θ(t) therefore may significantly depart from the ideal sinusoid. In the rotation signal θ(t) shown in FIG. 3a, for instance, the peak value increases at each iteration, meaning that the maximum tilt of the user's thigh gradually increases at each iteration. Furthermore, in the rotation signal θ(t) of FIG. 3a, instead of sharp minima, between two consecutive iterations a time gap is typically present, where the curve exhibits several ripples. Such ripples basically represent hesitations or freezing of the user 2 and/or failed attempts to lift the leg, which delay the execution of the next iteration.

During a subsequent step 202, the processing unit 3 preferably processes the received inertial data (e.g. from the gyroscope) so as to generate a further signal ω(t) (also termed herein after "velocity signal") indicative of the angular velocity of the sensing device 1 around an axis z perpendicular to the plane xy. As mentioned above, rotation of the sensing device 1 in the plane xy is the main movement of sensing device 1. Rotations of the sensing device 1 around the axis x and y are substantially negligible. Hence, the angular velocity of the sensing device 1 about those axes may accordingly be disregarded. According to some variants, also step 202 can be performed by the sensing device 1 itself, which accordingly provides to the processing unit 3 the velocity signal ω(t), instead of raw inertial data.

Figure 3B:
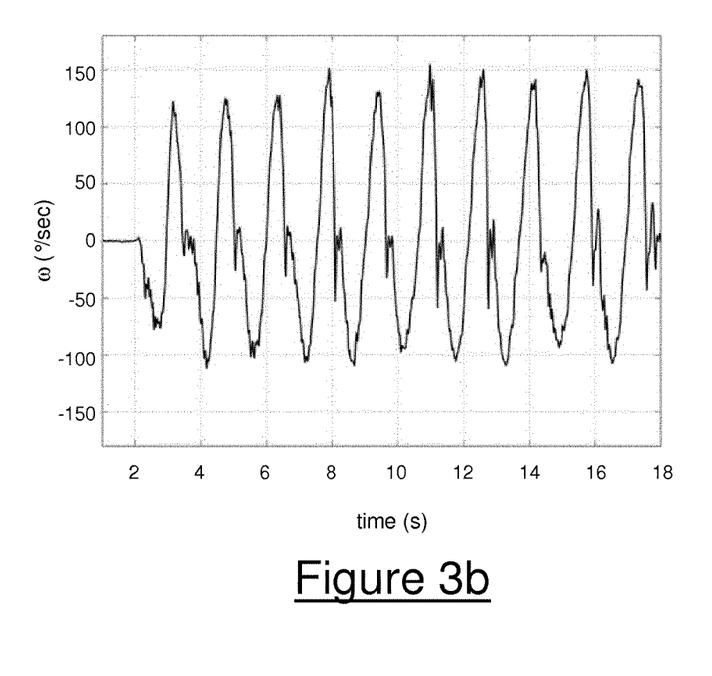

FIG. 3b schematically shows an exemplary velocity signal ω(t) as provided upon execution of step 202, relating to a sensing device 1 fixed to the thigh of a user 2 executing ten movement iterations of her/his thigh. Basically, the velocity signal ω(t) shown in FIG. 3b is the first derivative of the rotation signal θ(t). The velocity signal ω(t) exhibits positive and negative peaks where the leg reaches its maximum angular velocity, which occurs substantially half way between the minimum tilt position of the thigh (foot resting on the floor) and the maximum tilt position of the thigh (leg at its maximum height). The velocity signal ω(t) is instead equal to zero in correspondence of the minimum tilt positions and maximum tilt positions of the thigh. In principle (namely, in a healthy user), the velocity signal ω(t) would comprise no other zeros, in addition to those corresponding to the minimum and maximum tilt positions of the thigh. Instead, the velocity signal ω(t) shown in FIG. 3b comprises several other zeros, which are due to the movement anomalies (hesitations or freezing and/or failed attempts to lift the leg) of a patient with motor difficulties.

As the data from the sensing device 1 are received and the rotation signal θ(t) and the velocity signal ω(t) are reconstructed therefrom, the processing unit 3 preferably segments the rotation signal θ(t), namely it identifies in the reconstructed rotation signal θ(t) signal portions corresponding to the various iterations of the leg movement.

In particular, for each iteration, the processing unit 3 preferably determines:
  a start time $t_S$, namely the instant in which the user 2 started lifting her/his foot from the floor (minimum tilt position of the thigh);
  a peak time $t_P$, namely the instant in which the leg of the user 2 reached its maximum height (maximum tilt position of the thigh); and
  an end time $t_E$, namely the instant in which the foot of the user 2 was brought back the floor (minimum tilt position of the thigh).

To this purpose, at step 203, the processing unit 3 preferably identifies a number of null-velocity instants, namely all the instants t* subsequent to the last determined end time (namely, the end time of the iteration of the leg movement preceding the current one) in which the velocity signal ω(t) exhibits a zero, namely ω(t*)=0. In other words, at step 203 all the instants subsequent to the last determined end time are identified in which the leg of the user 2 does not move, independently of whether this is due to an anomaly or not. At this stage, such instants are all considered as candidates for being the start time $t_S$, end time $t_E$ or peak time $t_P$ of the current iteration.

Figure 4A:
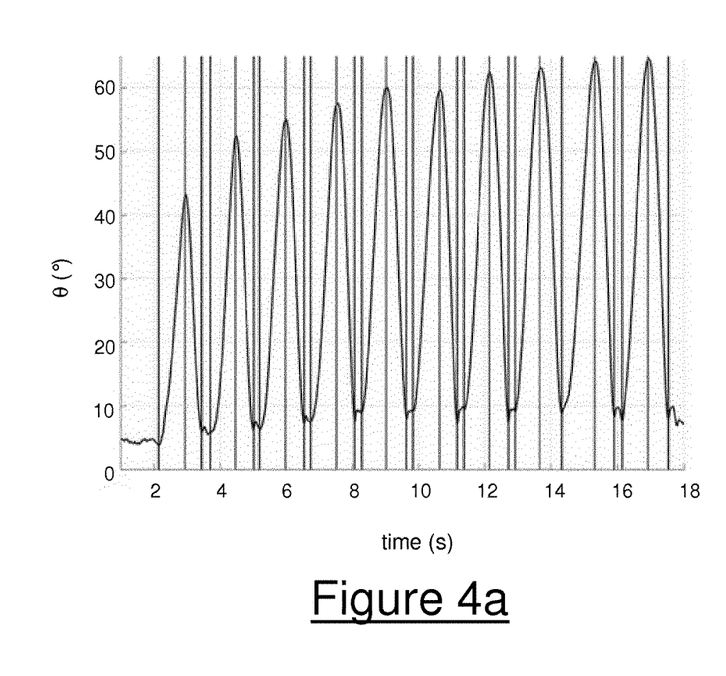
FIGS. 4a and 4b show the rotation signal and the velocity signal of FIGS. 3a and 3b during intermediate steps of the method according to embodiments of the present invention.
Figure 4B:
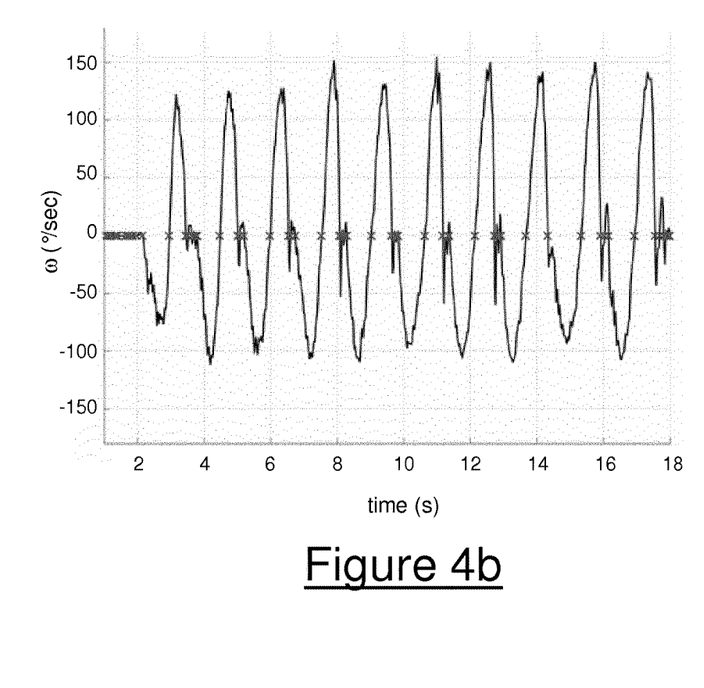

FIG. 4b shows the exemplary velocity signal ω(t) of FIG. 3b, wherein the null-velocity instants t* of the various iterations have been indicated by respective crosses. It shall be noticed that, for each iteration, several null-velocity instants t* are present.

Then, at a subsequent step 204, the processing unit 3 preferably classifies the null-velocity instants t* identified at step 203 in three groups:
candidate start/end times;
candidate peak times; and
transition times.

According to a preferred variant, at step 204 each null-velocity instant t* is assigned to a respective label ID, which indicates its classification. For instance, null-velocity instants t* classified as candidate start/end times are assigned to a label ID=−1, null-velocity instants t* classified as candidate peak times are assigned to a label ID=1, and null-velocity instants t* classified as transition times are assigned to a label ID=0. In order to classify each null-velocity instant t* (and hence to assign a proper label ID thereto), the processing unit 3 preferably checks conditions on relative values of the rotation signal θ(t) in correspondence of the null-velocity instants t*.

In particular, at step 204 the processing unit 3 preferably compares the value of the rotation signal θ(t) in correspondence of the null-velocity instant t*(i) to be classified with the values of the rotation signal θ(t) in correspondence of the preceding null-velocity instant t*(i−1) and/or next null-velocity instant t*(i+1). More particularly:

if θ(t*(i))<θ(t*(i−1)) and θ(t*(i))<θ(t*(i+1)), then the null-velocity instant t*(i) is classified as a candidate start/end time for the current iteration. If the null-velocity instant t*(i) is the first one identified, then it is compared only with the next null-velocity instant t*(i+1), namely it is only checked whether θ(t*(i))<θ(t*(i+1)). Moreover, if the null-velocity instant t*(i) is the last identified one, then it is compared only with the preceding null-velocity instant t*(i−1), namely it is only checked whether θ(t*(i))<θ(t*(i−1));

if θ(t*(i))>θ(t*(i−1)) and θ(t*(i))>θ(t*(i+1)), then the null-velocity instant t*(i) is classified as a candidate peak time for the current iteration;

else, the null-velocity instant t*(i) is classified as a transition time of the current iteration.

It shall be noticed that step 204 allows excluding from the list of candidates for being start time $t_S$, end time $t_E$ or peak time $t_P$ of the current iteration all the transition times, namely all the instants in which the leg of the user 2 temporarily stops due to a freezing or hesitation. However, step 204 still does not exclude from the list of candidates for being start time $t_S$, end time $t_E$ or peak time $t_P$ of the current iteration the relative maxima and relative minima of the rotation signal θ(t), which may be due e.g. to vibrations of the sensing device 1 or to failed attempts to lift the leg (the user 2 tries to lift her/his leg but then brings it down to the floor without completing the movement).

Then, at a subsequent step 205, the processing unit 3 preferably determines the start time $t_S$, peak time $t_P$ and end time $t_E$ of the current iteration amongst the candidate start/end times and the candidate peak times identified at step 204. To this purpose, at step 205 the processing unit 3 preferably determines start time $t_S$, end time $t_E$ and peak time $t_P$ of the current iteration as the combination of two candidate start/end times and one candidate peak time that fulfils one or more conditions on the values of the rotation signal θ(t) in correspondence of the candidate start/end times and candidate peak times. In particular, the start time $t_S$, peak time $t_P$ and end time $t_E$ are preferably selected as a combination of two candidate start/end times and one candidate peak time whose chronological order is such that the peak time lies between start time and end time, namely:

$$t_S < t_P < t_E \quad [1]$$

Figure 5:
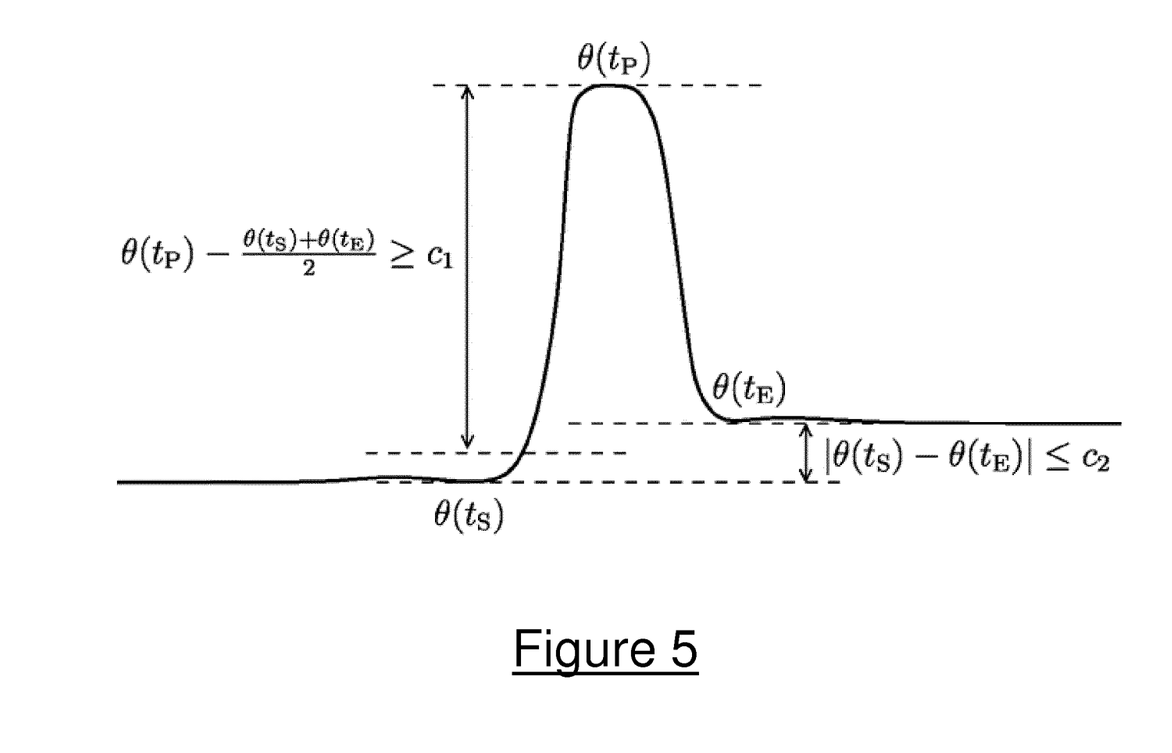
FIG. 5 shows a portion of the rotation signal substantially corresponding to a single iteration of the leg movement, wherein the conditions to be met by the start time, end time and peak time of the iteration are schematically depicted.

Furthermore, the combination of two candidate start/end times and one candidate peak time shall fulfil the following condition:

$$\theta(t_P) - \frac{\theta(t_S) + \theta(t_E)}{2} \geq c_1 \quad [2]$$

where c1 is a first threshold. FIG. 5 schematically provides a graphic representation of equation [2]. Basically, when the processing unit 3 checks that the combination of two candidate start/end times and one candidate peak time fulfils equation [2], it considers as a valid iteration only a thigh rotation whose angular amplitude (namely, the difference between the maximum tilt of the thigh and the minimum tilt of the thigh) exceeds or is equal to the first threshold c1. As the maximum tilt, the processing unit 3 considers the value of the rotation signal θ(t) in correspondence to the candidate peak time and, as the minimum tilt the processing unit 3 considers an average between the rotation signal θ(t) in correspondence to the two candidate start/end times.

This advantageously allows discarding relative maxima and minima of the rotation signal θ(t) which may be due e.g. to vibrations of the sensing device 1 or to failed attempts to lift the leg.

According to the present invention, the value of the first threshold c1 shall be selected large enough to avoid that vibrations of the sensing device 1 or failed attempts to lift the leg are improperly identified as the peak of the current iteration. On the other hand, the value of the first threshold c1 shall be low enough to avoid missing identification of the real peak of the current iteration (maximum tilt position of the thigh). Inventors have estimated that the first threshold c1 shall be preferably comprised between 7 and 13 degrees, more preferably between 9 and 11 degrees. For instance, the first threshold c1 may be equal to 10 degrees. Moreover, the combination of two candidate start/end times and one candidate peak time shall fulfil the following condition:

$$(\theta(t_S) - \theta(t_E)) c_2, \quad [3]$$

where c2 is a second threshold. FIG. 5 schematically provides a graphic representation also of equation [3]. Basically, when the processing unit 3 checks that the two candidate start/end times of the considered combination fulfil equation [3], it verifies if the current iteration starts and ends with a similar tilt of the thigh relative to the floor. At the beginning and at the end of each iteration, the user 2 shall indeed have her/his foot resting on the floor, meaning that the position of the leg (and in particular of the thigh) should be substantially the same, namely differ no more than c2.

The value of the second threshold c2 shall be preferably large enough to avoid considering several consecutive iterations as a single iteration. On the other hand, the value of the second threshold c2 shall be preferably small enough to avoid that a hesitation during an iteration is improperly identified as the start or the end of the current iteration. Inventors have estimated that the second threshold c2 shall be preferably comprised between 7 and 13 degrees, more preferably between 9 and 11 degrees. For instance, the second threshold c2 may be equal to 10 degrees.

The outcome of step 205 is shown in FIG. 4a. In particular, FIG. 4a shows the exemplary rotation signal θ(t) of FIG. 3a after segmentation. Specifically, in the rotation signal θ(t) of FIG. 4a, ten portions have been identified, namely one for each movement iteration. For each portion, the start time, peak time and end time determined for each iteration are marked by vertical lines. The first threshold c1 was equal to 10 degrees, and also the second threshold c2 was equal to 10 degrees.

Preferably, steps 203 to 205 are carried out in a substantially continuous way while the user 2 is executing the various iterations, thereby allowing identification of each single iteration immediately after it is completed. In particular, after determination of the end time of an iteration, the set of null-velocity instants t* relating to the current iteration starts being formed and is updated in real time by adding each new null-velocity instant t* as soon as it is identified based on the velocity signal ω(t) (step 203). Each new null-velocity instant t* is also classified in real time as a candidate start/end time, peak time or transition time, so that also the sets of candidates start/end times, peak times or transition times relating to the current iteration are updated in real time (step 204). Then, when a new null-velocity instant t* is identified and classified as either a candidate start/end time or a candidate peak time, the determination of the start time $t_S$, peak time $t_P$ and end time $t_E$ of the current iteration is preferably attempted as described above (step 205) on the last updated sets of candidates start/end times and peak times. The determination of the start time $t_S$, peak time $t_P$ and end time $t_E$ of the current iteration is completed when a combination of two candidate start/end times and one candidate peak time which fulfils the above described conditions is found.

If the data acquisition by the sensing device 1 is stopped before the start time $t_S$, peak time $t_P$ and end time $t_E$ are determined, all the null-velocity instants identified subsequently to the last determined end time are preferably discarded and the determination of the start time $t_S$, peak time $t_P$ and end time $t_E$ as per step 205 is stopped.

Further, if a start time $t_S$, peak time $t_P$ and end time $t_E$ for the current iteration can not be determined before a predetermined time gap has lapsed since determination of the end time for the last iteration, then it is assumed that the user 2 has completed the task iterations. Also in this case, preferably, the null-velocity instants identified subsequently to the last determined end time are discarded and the determination of the start time $t_S$, peak time $t_P$ and end time $t_E$ as per step 205 is stopped.

The processing unit 3 is therefore advantageously able to provide the segmentation outcome in real time, namely to isolate each single iteration following to the determination of the end time of the preceding one. It shall be indeed appreciated that the determination of start time, end time and peak time for each iteration does not involve use of any parameter relating to the other iterations. Hence, start time, end time and peak time of each iteration may be determined immediately after completion of the iteration, and will be no longer modified by the processing unit 3.

During a subsequent step 206 the processing unit 3 preferably uses at least one of the determined start time, end time and peak time for calculating one or more kinematic quantity of the movement of the user 2.

The kinematic quantity preferably comprise the speed of the leg movement, the amplitude of the leg movement, the duration of the leg movement, etc. calculated for each single movement iteration separately. This provides a real-time, quantitative evaluation of the performance of the user 2 in executing the movement or task, which e.g. enables an objective assessment of the seriousness of her/his pathology (e.g. an objective assessment of the UPDRS score, in case of Parkinson's disease).

For instance, at step 206 the processing unit 3 may calculate:
the angular amplitude $\theta\max(r)$ of the leg movement at the $r^{th}$ iteration;
the average angular speed $\Omega(r)$ of the leg movement at the $r^{th}$ iteration;
the time pause $T_{gap}(r)$ between the $r^{th}$ iteration and the preceding one;
the time $T_{peak}(r)$ lapsing between the peaks of the $r^{th}$ iteration and the preceding one.

These kinematic quantities are merely exemplary.

Preferably, the angular amplitude $\theta\max(r)$ of the leg movement at the $r^{th}$ iteration is calculated according to the following equation:

$$\theta\max(r) = \frac{\theta_A(r) + \theta_D(r)}{2} = \frac{(\theta(t_P(r)) - \theta(t_S(r))) + (\theta(t_P(r)) - \theta(t_E(r)))}{2}, \quad [4]$$

where $t_S(r)$ is the start time of the $r^{th}$ iteration, $t_P(r)$ is the peak time of the $r^{th}$ iteration, $t_E(r)$ is the end time of the $r^{th}$ iteration, $\theta_A(r)$ is the amplitude of the leg ascent movement and the $\theta_D(r)$ is the amplitude of the leg descent movement.

Preferably, the average angular speed $\Omega(r)$ of the leg movement at the $r^{th}$ iteration is calculated according to the following equation:

$$\Omega(r) = \frac{\theta_A(r) + \theta_D(r)}{D(r)} = \frac{(\theta(t_P(r)) - \theta(t_S(r))) + (\theta(t_P(r)) - \theta(t_E(r)))}{t_E(r) - t_S(r)} \quad [5]$$

where $D(r)$ is the duration of the leg movement at the $r^{th}$ iteration.

Preferably, the time pause $T_{gap}(r)$ between the $r^{th}$ iteration and the preceding one is calculated according to the following equation:

$$T_{gap}(r) = t_S(r) - t_E(r-1), \quad [6]$$

where $t_E(r-1)$ is the end time of the $(r-1)^{th}$ iteration.

Preferably, the time $T_{peak}(r)$ lapsing between the peaks of the $r^{th}$ iteration and the preceding one is calculated according to the following equation:

$$T_{peak}(r) = t_P(r) - t_P(r-1), \quad [7]$$

where $t_P(r-1)$ is the peak time of the $(r-1)^{th}$ iteration.

Figure 6A:
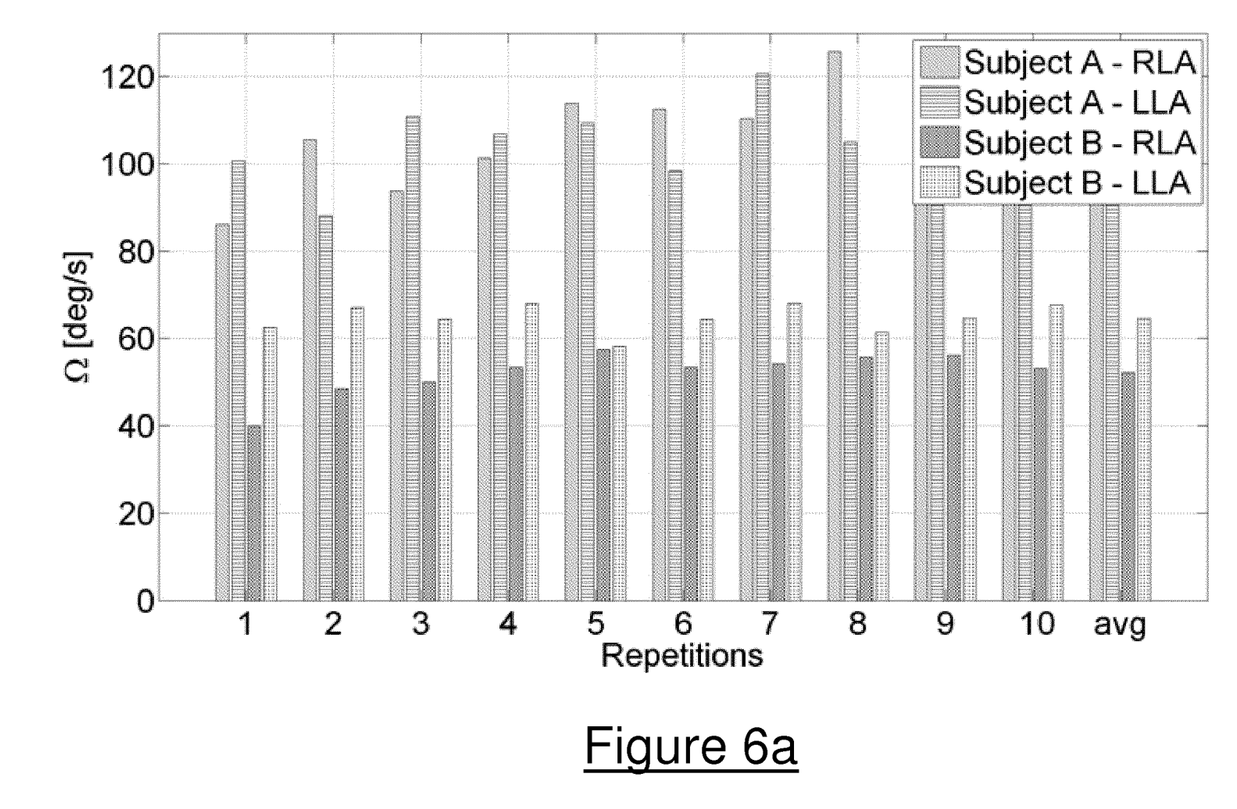
FIGS. 6a, 6b, 6c show graphs of a comparative test carried out on a healthy user and a user affected by the Parkinson's disease, by applying the method according to an embodiment of the present invention
Figure 6B:
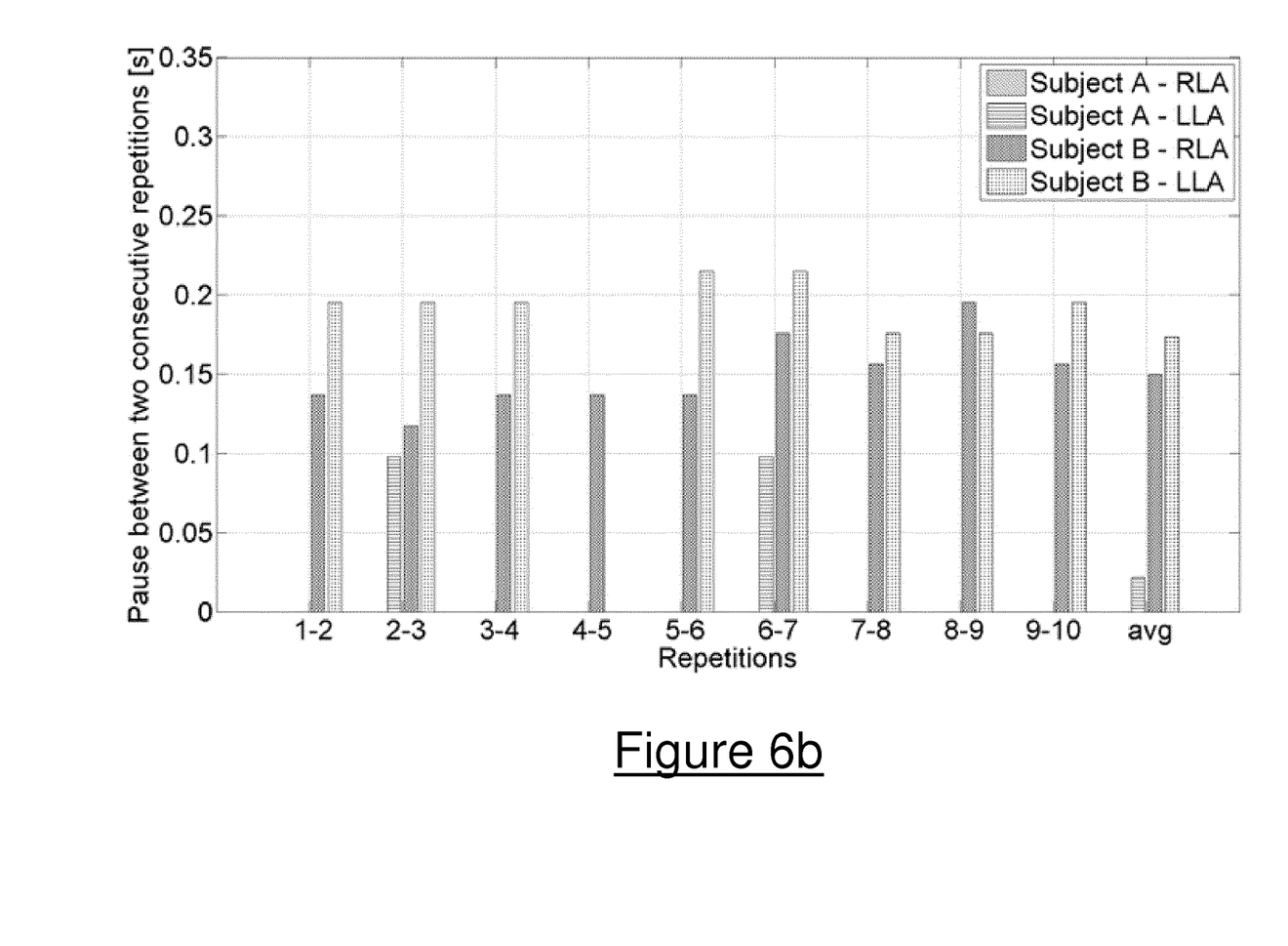
Figure 6C:
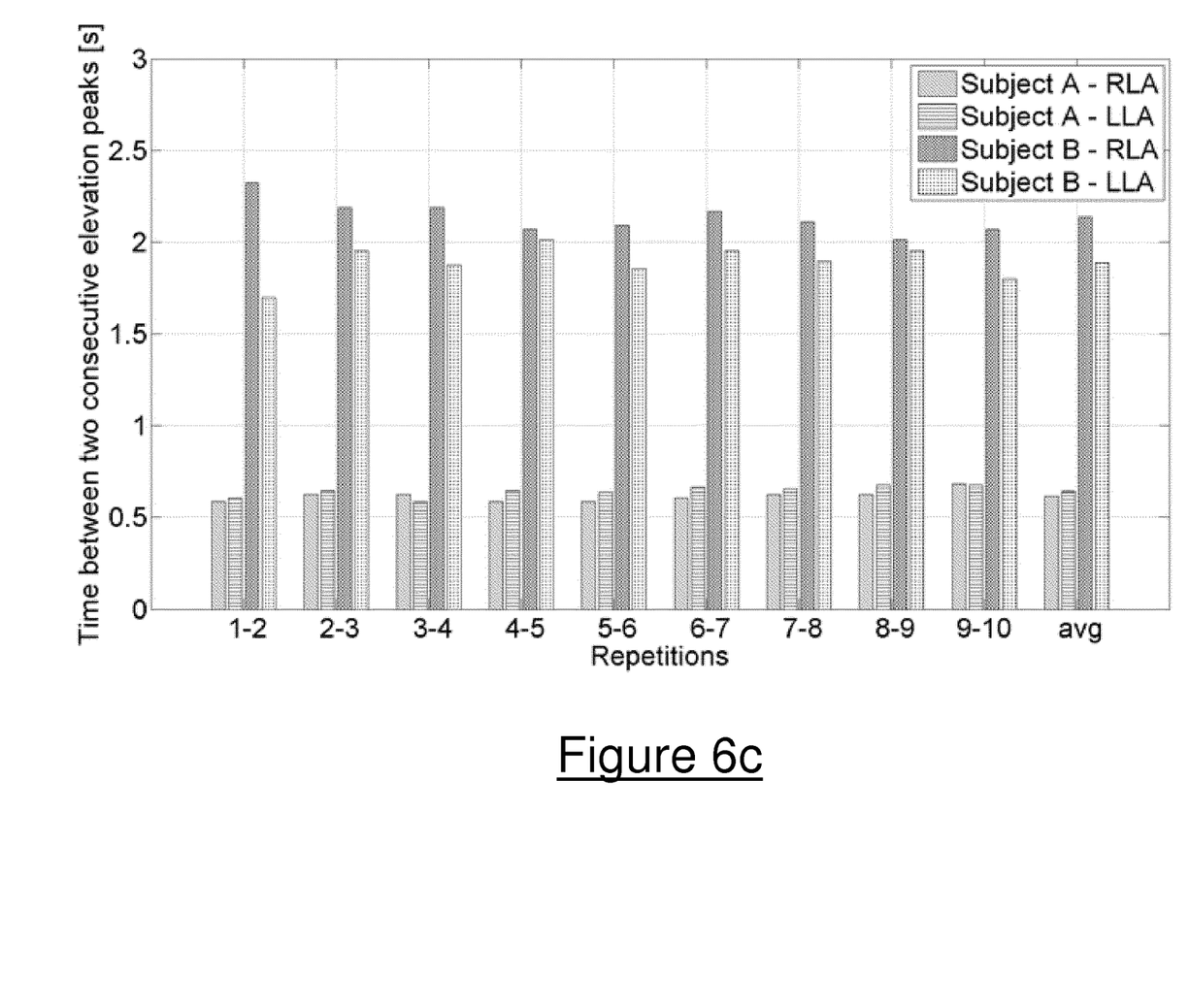

The graphs of FIGS. 6a, 6b and 6c show the results of a comparative analysis of the Leg Agility task carried out on a healthy user ("Subject A") and a patient affected by the Parkinson's disease ("Subject B"), in terms of the above kinematic quantities average angular speed (FIG. 6a), time pause between consecutive iterations (FIG. 6b) and time lapsing between peaks of consecutive iterations (FIG. 6c). Each graph shows the results for both the right leg (label "RLA") and the left leg (label "LLA").

From the graphs, it is apparent that the average angular speed for the healthy user is significantly higher than for the patient affected by the Parkinson's disease (see FIG. 6a), the time pause between consecutive iterations is substantially negligible for the healthy user while it is quite long for the patient affected by the Parkinson's disease (see FIG. 6b), and the time lapsing between peaks of consecutive iterations amplitude for the healthy user is significantly shorter than for the patient affected by the Parkinson's disease (see FIG. 6c).

Step 206 may also comprise the automatic assignment of a score (e.g. a UPDRS score) to the user 2, e.g. based on the values of the calculated kinematic quantities.

The raw sensed data provided by the sensing device 1 at step 200 and/or the rotation/velocity signals calculated at steps 201/202, and/or the start/end/peak times calculated at step 205 and/or the kinematic quantities calculated at step 206 (and/or the assigned score derived therefrom) are preferably transmitted by the processing unit 3 to the remote database 4 via the communication network 5. In this way, all such information are available and may be accessed by a neurologist or specialized personnel, e.g. for statistic purposes and/or for tuning the drug dosage to user 2.

Though in the above description it has been assumed that all the method steps shown in FIG. 2 are carried out by the same processing unit 3, this is not limiting. According to some variants, a processing unit 3 (located at the premises of the user 2, e.g. in its personal computer) may perform e.g. up to step 202, and then transmit the rotation and velocity signals via the communication network 5 to a cloud computing architecture, whose processing units carry out the subsequent steps. According to other variants, the local processing unit 3 may perform e.g. up to step 205, and then transmit the start/end/peak times via the communication network 5 to the cloud computing architecture, whose processing units carry out the subsequent steps.

Though the above detailed description has been made with reference to the leg movements, this is not limiting. It may indeed be appreciated that the method according to the present invention is straightforwardly applicable to the movement of any limb or body part, provided that the movement comprises one or more rotations of the limb or body part substantially in a plane.

Hence, the above described method advantageously allows measuring the kinematic quantities of the movement of a limb of a user in a fully automated way and in real-time. This advantageously allows the user 2 to carry out the measurement as often as necessary at home in an autonomous way, thereby enabling a more frequent monitoring of her/his health condition.

The results of the method are very accurate, in spite of the anomalies which typically affect the users movements. The method described above is indeed capable of properly segmenting (namely, identifying and isolating) each single iteration of the movement, even when several relative maxima and minima due to such anomalies are present in the signals provided by the sensing device attached to the user's limb. Hence, the values of the kinematic quantities calculated based on such segmentation are very accurate and reliable.

The invention claimed is:

1. An autonomous method for monitoring the movement of a part of a human body, said movement comprising a number N of iterations of a rotation of said part of said human body in a plane (xy), said method comprising:
    providing, with a sensing device, data indicative of said movement of said part of said human body;
    processing, with a processor, said data to generate a rotation signal ($\theta(t)$) indicative of said rotation of said part of said human body in said plane (xy); and
    identifying, with the processor, a portion of said rotation signal ($\theta(t)$) corresponding to a respective iteration of said rotation of said part of said human body in said plane (xy) by determining a start time ($t_S$), an end time ($t_E$) and a peak time ($t_P$) of said respective iteration;
    said determining comprising:
    determining, with the processor, a plurality of null-velocity instants ($t^*$) wherein an angular velocity of said part of said human body in said plane (xy) is substantially null;
    determining, with the processor and amongst said plurality of null-velocity instants ($t^*$), a set of candidate start/end times and a set of candidate peak times on the basis of at least one condition on relative values of said rotation signal ($\theta(t)$) in correspondence of said plurality of null-velocity instants ($t^*$); and
    determining, with the processor, said start time ($t_S$), said end time ($t_E$) and said peak time ($t_P$) as a combination of two candidate start/end times and a candidate peak time that fulfils at least one condition on values of said rotation signal ($\theta(t)$) in correspondence of said candidate start/end times and said candidate peak times,
    wherein said determining said start time ($t_S$), said end time ($t_E$), and said peak time ($t_P$) includes finding said combination of said two candidate start/end times and said candidate peak time such that a difference between a value of the rotation signal ($\theta(t)$) corresponding to the candidate peak time and an average between the values of the rotation signal ($\theta(t)$) corresponding to the two candidate start/end times exceeds or is equal to a first threshold ($c1$).

2. The method according to claim 1, wherein said data comprise:
    first inertial data provided by an accelerometer of said sensing device cooperating with said part of said human body;
    second inertial data provided by a gyroscope of said sensing device; and
    magnetic data provided by a magnetometer of said sensing device.

3. The method according to claim 2, further comprising:
    if a norm of an acceleration detected by said accelerometer is lower than a predetermined threshold, processing said first inertial data and said magnetic data to generate said rotation signal ($\theta(t)$); and
    if the norm of an acceleration detected by said accelerometer is higher than said predetermined threshold, processing said second inertial data to generate said rotation signal ($\theta(t)$).

4. The method according to claim 1, wherein said determining said set of candidate start/end times and said set of candidate peak times comprises classifying each null-velocity instant ($t^*(i)$) as either one of the candidate start/end time or said candidate peak time by comparing the value of said rotation signal ($\theta(t)$) in correspondence of said null-velocity instant ($t^*(i)$) to be classified with the value of said rotation signal ($\theta(t)$) in correspondence of a further null-velocity instant ($t^*(i-1)$, $t^*(i+1)$) preceding or succeeding said null-velocity instant ($t^*(i)$) to be classified.

5. The method according to claim 4, wherein said determining said set of candidate peak times amongst said plurality of null-velocity instants ($t^*$) comprises classifying said null-velocity instant ($t^*(i)$) as a candidate peak time if $\theta(t^*(i))>\theta(t^*(i-1))$ and $\theta(t^*(i))>\theta(t^*(i+1))$.

6. The method according to claim 4, wherein said determining said set of candidate start/end times amongst said plurality of null-velocity instants ($t^*$) comprises classifying said null-velocity instant ($t^*(i)$) as one of the candidate start/end time if:
    $\theta(t^*(i))<\theta(t^*(i+1))$, in case said null-velocity instant ($t^*(i)$) is a first null-velocity instant identified subsequently to a last determined end time;
    $\theta(t^*(i))<\theta(t^*(i-1))$, in case said null-velocity instant ($t^*(i)$) is a last null-velocity instant identified; and
    $\theta(t^*(i))<\theta(t^*(i-1))$ and $\theta(t^*(i))<\theta(t^*(i+1))$ for any other null-velocity instant ($t^*(i)$).

7. The method according to claim 1, wherein said determining said start time ($t_S$), said end time ($t_E$) and said peak time ($t_P$) comprises finding said combination of said two candidate start/end times and said candidate peak time whose chronological order is such that said peak time ($t_P$) lies between said start time ($t_S$) and said end time ($t_E$).

8. The method according to claim 7, wherein said determining said start time ($t_S$), said end time ($t_E$) and said peak time ($t_P$) comprises finding said combination of said two candidate start/end times and said candidate peak time which fulfils the following condition:

$$\theta(t_P) - \frac{\theta(t_S) + \theta(t_E)}{2} \geq c_1$$

where $c1$ is the first threshold.

9. The method according to claim 8, wherein said determining said start time ($t_S$), said end time ($t_E$) and said peak time ($t_P$) comprises finding said combination of said two candidate start/end times which fulfils the following condition:

$$(\theta(t_S) - \theta(t_E)) \leq c_2$$

where c2 is a second threshold.

10. The method according to claim 9, wherein said second threshold is between 7 and 13 degrees.

11. The method according to claim 1, wherein said identifying a portion of said rotation signal ($\theta(t)$) corresponding to said respective iteration of said rotation of said part of said human body in said plane (xy) is started while said respective iteration is being executed by said part of said human body, after an end time for an iteration preceding said respective iteration has been determined.

12. The method according to claim 11, wherein:
said determining said plurality of null-velocity instants ($t^*$) comprises forming a set of null-velocity instants ($t^*$) subsequent to said end time of said preceding iteration, and updating it by adding thereto each new null-velocity instant ($t^*$) subsequent to said end time of said preceding iteration, when said new null-velocity instant ($t^*$) is identified;
said determining said set of candidate start/end times and said set of candidate peak times comprises classifying said new null-velocity instant ($t^*$) as one of the candidate start/end times or as the candidate peak time, when said new null-velocity instant ($t^*$) is identified; and
said determining said start time ($t_S$), said end time ($t_E$) and said peak time ($t_P$) comprises seeking for said combination of said two candidate start/end times and one said candidate peak time which fulfils said at least one condition, when said new null-velocity instant ($t^*$) is classified as either one of the candidate start/end times or the candidate peak time.

13. The method according to claim 12 wherein, if said sensing device stops providing said data indicative of said movement, said determining said start time ($t_S$), said end time ($t_E$) and said peak time ($t_P$) is stopped and said null-velocity instants ($t^*$) subsequent to said end time of said preceding iteration are discarded.

14. The method according to claim 12 wherein, if said start time ($t_S$), said end time ($t_E$) and said peak time ($t_P$) are not determined before a predetermined time gap has lapsed since said end time of said preceding iteration, said determining said start time ($t_S$), said end time ($t_E$) and said peak time ($t_P$) is stopped and said null-velocity instants ($t^*$) subsequent to said end time of said preceding iteration are discarded.

15. The method according to claim 1, wherein said processing said data to generate said rotation signal ($\theta(t)$) comprises filtering said data through an orientation estimation filter providing as outPut a 4-dimensional array representing an orientation of said sensing device in a 3D space, and deriving said rotation signal ($\theta(t)$) from said 4-dimensional array.

16. The method according to claim 15, wherein said orientation estimation filter is a Kalman filter.

17. The method according to claim 1, wherein said first threshold is between 7 and 13 degrees.

18. An autonomous system for monitoring the movement of a part of a human body, said movement comprising a number N of iterations of a rotation in a plane (xy) of said part of said human body, said system comprising:

a sensing device configured to cooperate with said part of said human body and provide data indicative of said movement of said part of said human body; and
a processor configured to process said data to generate a rotation signal ($\theta(t)$) indicative of said rotation of said part of said human body in said plane (xy) and to identify a portion of said rotation signal ($\theta(t)$) corresponding to a respective iteration of said rotation of said part of said human body in said plane (xy) by determining a start time ($t_S$), an end time ($t_E$) and a peak time ($t_P$) of said respective iteration, said determining comprising:
determining a plurality of null-velocity instants ($t^*$) wherein an angular velocity of said part of a human body in said plane (xy) is substantially null;
determining, amongst said plurality of null-velocity instants ($t^*$), a set of candidate start/end times and a set of candidate peak times on the basis of at least one condition on relative values of said rotation signal ($\theta(t)$) in correspondence of said plurality of null-velocity instants ($t^*$); and
determining said start time ($t_S$), said end time ($t_E$) and said peak time ($t_P$) as a combination of two candidate start/end times and a candidate peak time that fulfils at least one condition on values of said rotation signal ($\theta(t)$) in correspondence of said candidate start/end times and said candidate peak times,
wherein said determining said start time ($t_S$), said end time ($t_E$), and said peak time ($t_P$) includes finding said combination of said two candidate start/end times and said candidate peak time such that a difference between a value of the rotation signal ($\theta(t)$) corresponding to the candidate peak time and an average between the values of the rotation signal ($\theta(t)$) corresponding to the two candidate start/end times exceeds or is equal to a first threshold (c1).

19. A non-transitory computer-readable medium encoded with computer-readable instructions that, when executed by a computer, cause the computer to perform an autonomous method for monitoring the movement of a part of a human body, said movement comprising a number N of iterations of a rotation of said part of said human body in a plane (xy), the method comprising:
receiving, from a sensing device, data indicative of said movement of said part of said human body;
processing said data to generate a rotation signal ($\theta(t)$) indicative of said rotation of said part of a human body in said plane (xy); and
identifying a portion of said rotation signal ($\theta(t)$) corresponding to a respective iteration of said rotation of said part of said human body in said plane (xy) by determining a start time ($t_S$), an end time ($t_E$) and a peak time ($t_P$) of said respective iteration;
said determining comprising:
determining a plurality of null-velocity instants ($t^*$) wherein an angular velocity of said part of said human body in said plane (xy) is substantially null;
determining, amongst said plurality of null-velocity instants ($t^*$), a set of candidate start/end times and a set of candidate peak times on the basis of at least one condition on relative values of said rotation signal ($\theta(t)$) in correspondence of said plurality of null-velocity instants ($t^*$); and
determining said start time ($t_S$), said end time ($t_E$) and said peak time ($t_P$) as a combination of two candidate start/end times and a candidate peak time that fulfils at least one condition on values of said rotation signal ($\theta(t)$) in correspondence of said candidate start/end times and said candidate peak times, wherein said determining said start time ($t_S$), said end time ($t_E$), and said peak time ($t_P$) includes finding said combination of said two candidate start/end times and said candidate peak time such that a difference between a value of the rotation signal ($\theta(t)$) corresponding to the candidate peak time and an average between the values of the rotation signal ($\theta(t)$) corresponding to the two candidate start/end times exceeds or is equal to a first threshold ($c1$).

* * * * *